United States Patent [19]

Rizk et al.

[11] Patent Number: 4,639,244
[45] Date of Patent: Jan. 27, 1987

[54] IMPLANTABLE ELECTROPHORETIC PUMP FOR IONIC DRUGS AND ASSOCIATED METHODS

[75] Inventors: Nabil I. Rizk, 229 Haymont Dr., Gibsonia, Pa. 15044; Charles L. Stevens, Pittsburgh, Pa.

[73] Assignee: Nabil I. Rizk, Gibsonia, Pa.

[21] Appl. No.: 754,629

[22] Filed: Jul. 12, 1985

Related U.S. Application Data

[63] Continuation of Ser. No. 491,241, May 3, 1983, abandoned.

[51] Int. Cl.[4] .............................................. A61N 1/30
[52] U.S. Cl. ..................................... 604/19; 604/891; 604/151
[58] Field of Search .................. 604/20, 21, 19, 140, 604/145, 150, 891–897, 151; 204/299 R

[56] References Cited

U.S. PATENT DOCUMENTS

| | | | |
|---|---|---|---|
| 3,539,455 | 11/1970 | Clark | 204/1 |
| 3,765,414 | 10/1973 | Arlen | 128/260 |
| 3,894,538 | 7/1975 | Richter | 128/260 |
| 3,926,188 | 12/1975 | Baker et al. | 128/260 |
| 3,993,072 | 11/1976 | Zaffaroni | 128/260 |
| 4,019,510 | 4/1977 | Ellis | 604/20 |
| 4,055,175 | 10/1977 | Clemens et al. | 128/213 |
| 4,140,121 | 2/1979 | Kühl et al. | 128/260 |
| 4,140,122 | 2/1979 | Kühl et al. | 128/260 |
| 4,350,155 | 9/1982 | Thompson | 128/213 R |
| 4,360,019 | 11/1982 | Portner et al. | 128/213 R |
| 4,364,385 | 12/1982 | Lossef | 128/213 R |

OTHER PUBLICATIONS

"A Totally Implantable Drug Infusion Device: . . . Insulin Infusion", Buchwald et al., Diabetes Care, 1980.
"A Two-Phase Fluid . . . Temperature Variability", Dormen et al., Trans. Am. Soc. Artif. Intern. Organs., 1981.
"Implantable Drug-Delivery Systems," Blackshear.
Electronic Flow Rate . . . Infusion Pump, Fergusen et al., Diabetes Care, 1980.

Primary Examiner—Edward M. Coven
Assistant Examiner—Max F. Hindenburg
Attorney, Agent, or Firm—Arnold B. Silverman

[57] ABSTRACT

An implantable electrophoretic pump for ionic drugs and the method of using the same is provided. A reservoir is provided with a filler opening and a discharge opening. The discharge opening has a diffusion membrane and a pair of associated electrodes. A battery and electronic components provide for energizing the electrodes so as to effect ion transfer of the ionic drugs into other portions of the patient's body through the voltage induced between the two electrodes. The pump is particularly useful for ionic drugs such as insulin, blood thinners, antibiotics and the like. A method of making a porous electrode.

48 Claims, 15 Drawing Figures

IMPLANTABLE ELECTROPHORETIC PUMP FOR IONIC DRUGS AND ASSOCIATED METHODS

This is a continuation of application Ser. No. 491,241, filed May 3, 1983, now abandoned.

BACKGROUND OF THE INVENTION

1. Field of the Invention

This invention relates to an implantable, molecular electrophoretic pump for ionic drugs and, more specifically, it relates to a durable and improved pump which is adapted to supply, on a predetermined basis, desired quantities of medication.

2. Description of the Prior Art

It has been known that medicines may, in many instances, be employed more efficiently by providing a pump to deliver the medication to a patient at a more uniform rate than would be experienced by periodic injections through syringes. Such pumps have been provided with the capability of either being mounted externally of the body or implanted in the body. See generally Electronic Flow Rate Controller for Portable Insulin Infusion Pump by R. T. Ferguson et al., Diabetes Care, Vol. 3 No. 2, March-April 1980 pp. 332-337; A Totally Implantable Drug Infusion Device: Laboratory and Clinical Experience Using a Model With Single Flow Rate and New Design for Modulated Insulin and Infusion by Henry Buchwald et al., Diabetes Care, Vol. 3 No. 2, March-April 1980, pp. 351-358; Implantable Drug-Delivery Systems by Perry J. Blackshear pp. 66-73, Scientific American 241 (December 1979); and H. Buchwald, A Two-Phase Fluid Powered Insulin Infusion Pump with Basal/Bolus Capability Which Compensates for Pressure and Temperature Variability, Trans. Am. Soc. Artif. Internal Organs, 27, 263-40 (1981).

U.S. Pat. Nos. 3,894,538 and 4,140,122 disclose multichambered medicine supplying pumps which involve actual transfer of solution and require the use of moving parts.

U.S. Pat. No. 4,140,121 discloses an implantable dosing device which delivers drugs plus liquid and involves a variable volume medicine reservoir and a liquid chamber which is subjected to variations in volume through transport of liquid by electroosmosis.

One of the problems experienced with the prior art systems has been the need to use a system having movable parts, thus rendering the pump susceptible to breakdowns and also requiring large power consumption.

In spite of the foregoing teachings, there remains a need for a self-contained, refillable, externally programmable, implantable drug infusion device.

SUMMARY OF THE INVENTION

The present invention has solved the above-described problems by providing a self-contained, refillable, externally programmable, implantable ionic drug dispensing electrophoretic pump. It provides a sealed housing and a reservoir having filler and discharge openings. The filler opening may be sealed by a self-sealing member which is adapted to be pierced by a reservoir charging instrument, such as a hypodermic needle. The discharge opening is adapted to permit the flow of ions therethrough. The discharge opening preferably has a passive diffusion membrane and a pair of associated electrodes. Battery means energize the electrodes and cooperate with electronic means so as to provide delivery of ions at the desired rate.

In one embodiment of the invention, diffusion will be the principal source of ion distribution during periods when electrodes are not energized. When the electrodes are energized, depending upon the polarity of the electrodes as compared with the nature of the ion, the rate of flow by diffusion will either be enhanced or retarded. Also, in a preferred embodiment the amount of flow initiated by energizing the electrodes can be increased for periods of unusual need.

The invention also encompasses a method for accomplishing distribution of ionic drugs.

It is an object of the present invention to provide a reliable means for delivering efficiently, predetermined quantities of an ionic medication by means of an implantable pump.

It is a further object of the invention to provide such a pump and a method of using the same wherein durability and dependability of the pump are enhanced as a result of the absence of moving parts.

It is another object of the present invention to provide such an implantable pump which may be programmed externally.

It is a further object of the present invention to provide such a pump which requires very modest electrical energy to operate in the predetermined manner.

It is yet another object of the invention to provide such a pump which may have its reservoir replenished by means of a hypodermic needle without the need for a surgical procedure.

It is a further object of the present invention to provide such a pump which is adapted to be used with a number of different types of ionic drugs.

It is a further object of the present invention to provide such a pump which is adapted to be employed in the delivery of insulin to diabetic patients.

It is yet another object of the invention to provide means for delivering an extra dose of the medication during periods of unique needs.

These and other objects of the invention will be more fully understood from the following description of the invention on reference to the illustrations appended hereto.

DESCRIPTION OF THE PREFERRED EMBODIMENTS

As used herein, the term "ionic drug" means ionically charged materials adapted for medical uses within a human or animal and shall expressly include, but not be limited to, insulin, peptide hormones, blood thinners, neurotrophics, antibiotics, analgesics, immunosuppresive agents and pharmaceutical materials modified to carry a charge.

As used herein the term "patient" shall be deemed to include humans and animals.

Figure 1:
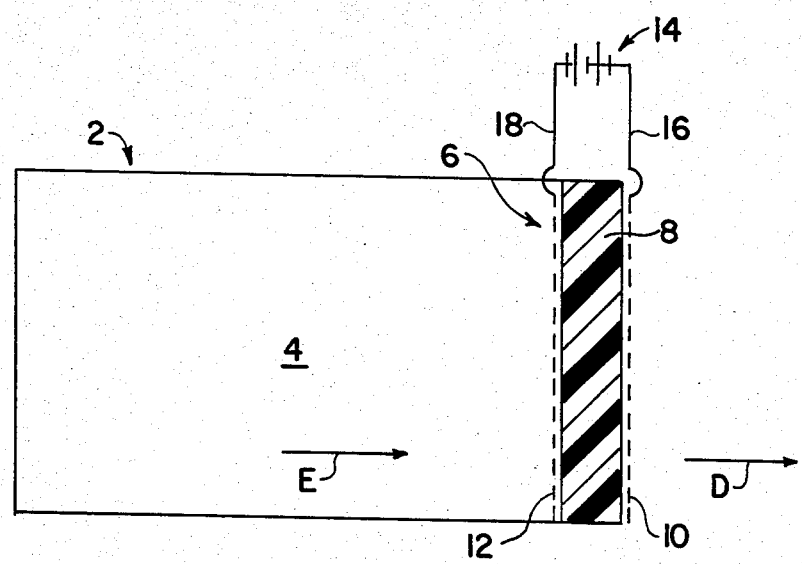
FIG. 1 is a schematic illustration of a principle of the present invention.

Referring now to FIG. 1 in greater detail there is shown schematically a reservoir of the present invention and the manner in which the ionic drugs will be passed through the discharge opening so as to emerge from the pump and be delivered to the patient for absorption. The reservoir 2 is hermetically sealed and has a reservoir chamber 4 which contains the ionic drug or drugs to be dispensed. The drugs may conventionally be in the form of a suspension. Discharge opening 6 is provided with a passive membrane 8 which will permit ions to pass therethrough. This membrane 8 preferably also resists passage of bacteria therethrough. The membrane 8 may be a cellulose membrane. Among the preferred materials that are suitable for use as the membrane 52 are those made from cellulose esters, nylon polyvinylidene flouride, polytetrafluoroethylene, cellulose nitrate and acetate and mixtures thereof. The preferred membranes have pore sizes from about 0.025 to 8 microns and are from about 100 to 200 microns thick. The membrane diameters are preferably between about 13 and 293 millimeters. In general, many types of microfiltration membranes may be employed. Among the preferred materials are those sold under the trade designations "MF" (Millipore); "Celotate" (Millipore); "Durapore" (Millipore); "Diaflow" (Amicon); "Mitex" (Millipore); and "Fluoropore" (Millipore).

The electodes are preferably composed of a material selected from the group consisting of silver/silver chloride, carbon, carbon mesh and platinum.

Disposed on opposite sides of the membrane 8 and operatively associated therewith are a pair of porous electrodes 10, 12 which will be described in greater detail hereinafter. A battery 14, by means of anode lead 16 and cathode lead 18, energizes the respective electrodes 10, 12. In this arrangement, if insulin were contained within the chamber 4, as insulin is a negative ion, the membrane 8 will permit passage of the ions through the same. The direction of movement caused by electrophoresis with the electrodes energized as shown is indicated by the arrow "E".

Under normal circumstances, the buildup of concentration of ions in the reservoir 4 will result in passage of the material through the membrane 8 in the direction indicated by the arrow "D" even when the electrodes are not energized. This diffusion flow may be relied upon, in some instances, as establishing a basic rate for ongoing delivery of the ionic drugs. In some cases, as may be true with insulin, it may be desirable to provide a greater flow than would occur through diffusion in which case energizing the electrodes 10, 12 serves to increase the rate of delivery of the material. If desired, for certain materials, means may be provided for reversing remotely the polarity of electrodes 10, 12 thereby causing the electrophoresis to retard the amount of ionic flow effected through diffusion.

EXAMPLE

In order to provide further understanding of the invention the following example is provided.

Figure 4:
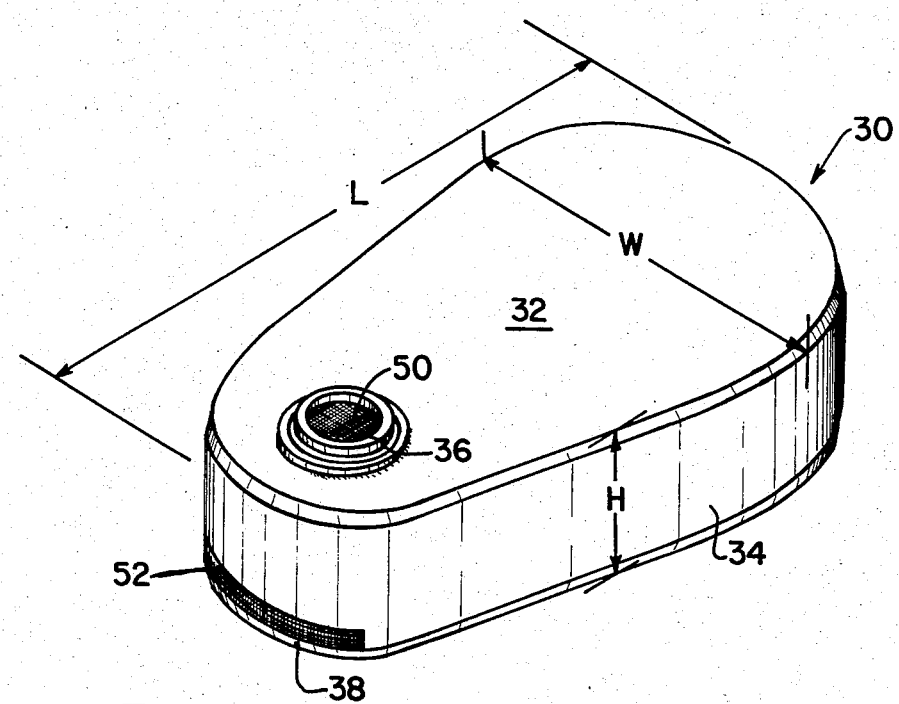
FIG. 4 is a perspective view of a form of pump of the present invention.

A housing, made of titanium, having the shape illustrated in FIG. 4 is provided. The housing has a height H of about 18 mm., a length L of about 10 cm, an average width W of about 40 mm and a wall thickness of about 0.5 mm. The reservoir is made of titanium and has a continuous interior coating of silicone rubber about 1/10 mm. thick. The reservoir is cylindrical in shape with a diameter of about 35 mm. and an average height of about 19 mm. The reservoir is secured in the housing and has about 1 gram of insulin in slurry form in its chamber. The insulin may be crystalline insulin suspended in NaCl based buffer with extra crystals suspended in a matrix of trimethyl cellulose. The total insulin is present (slurry plus undissolved solid) in quantities of about 25 mg/ml and the reservoir holds about 25 ml. A unit of insulin weighs about 1/24 mg.

Two 2.7 volt lithium iodide batteries energize a pair of carbon mesh porous electrodes which are on opposite sides of a cellulose acetate passive membrane having a thickness of about 150 microns and a cross sectional area of about 0.5 cm$^2$. A voltage of about 1.2 volts is imposed across the electrodes. Direct current or pulsed direct current are preferably employed. The filler membrane is composed of reinforced silicone rubber and has an area of about 1½ cm$^2$.

The system, when the electrodes are energized, operates at about 1–15 milliamperes.

The electronic unit turns the pump on and off during predetermined periods with diffusion induced flow continuing at a basic rate when the electrodes are not on.

Before turning to further details of the invention, the background will be considered. The electrophoretic ion pump utilizes the phenomenon of electrodiffusion for the transport of an ionic drug from a reservoir to the surrounding body tissue. The phenomenon involves a combination of diffusion and electrophoretic transport.

Solutions consist of molecules dissolved in a solvent. It sometimes is convenient to regard one or more components as solute and the other the solvent. Both solvent and solute molecules are in constant motion with respect to each other and in constant collision, as long as the solution remains liquid. If an interface is formed between the solution and pure liquid solvent and if this interface remains stable, solute molecules will be transported across the interface from solution to solvent. This process, if left undisturbed, will continue until the concentration of solute becomes the same throughout. Net transport will cease, and the system will be in equilibrium. This mode of transport is called "free diffusion".

Sometimes in the process of free diffusion, it is difficult to stabilize the interface between solution and solvent. Because this can be troublesome, a porous membrane is sometimes placed between solution and the solvent, forming the interface. Diffusion, then, takes place within the pores of the membrane. Although the rate of transport is usually diminished, the phenomenon is still basically diffusion.

If the solute molecules happen to be larger than the pores of the membrane, they are excluded and will be retained in the solution side of the boundary. If there is a mixture of molecules both larger and smaller than the pores, the smaller ones will pass through the membrane and the larger ones will be retained. In the electrophoretic ion pump, the membrane will pass the solvent (water) of body fluids, te inorganic salts, organic acids, sugars and most proteins. As only the ionic drug will be supplied within the reservoir, all these components of body fluids will quickly equilibrate with the reservoir so there will be no or little net transport of these substances of body fluids during operation of the pump. This concept will be referred to herein as employing a membrane which will readily pass the ionic drug therethrough. The pump of the present invention may be considered a molecular pump as distinguished from a bulk pump. The pump has pressure equilibrium with the result that it does not induce the flow of fluids.

The process of diffusion is basically the same for molecules that carry no net electrical charge as for ions. With respect to molecules that are capable of penetrating the membrane, if their rates of diffusion are diminished to the same extent, the membrane is said to be passive. If, on the other hand, the membrane affects different kinds of molecules to different extents, the membrane is permselective (or an "active membrane"). The most common kind of permselectivity arises with ionic solute molecules and immobilized electric charges in or near the pores of the membrane. In this case, the ion carrying a charge of the same sign as the immobilized ones will be inhibited or excluded from the membrane. The ion carrying a charge of the opposite sign will be transported with little or no inhibition. The pump of the present invention preferably utilizes a passive membrane, but permselective membranes may be used for transport of particular ionic drugs.

It is generally not satisfactory to rely solely on the process of diffusion for a drug delivery system. This is because the rate of delivery depends upon the physical and mechanical properties of the membrane which are not alterable conveniently. This means that one has virtually no control of the drug delivery rate. In the case of insulin delivery, moreover, the pump may have to operate at two different delivery rates, changing from one to the other several times a day such as meals, for example. If the drug molecules are ions, however, delivery can also be achieved through electrophoresis.

Electrophoresis can be best understood in terms of an example. Consider a pair of parallel flat electrodes immersed in a solution containing ions. If a certain voltage is applied to the electrodes, a current will flow in the space between them. The ions in solution move, those with positive charge moving toward the cathode (cations) and those with negative charge moving toward the anode (anions). This flow of ions constitutes a flow of electric current. The rate of flow of the ions depends on the sign and magnitude of the electric charge that they carry, the physical size of the ion, the voltage placed across the cell, and the distance of separation of the electrodes. Because some of these properties are properties of the apparatus and not the molecule being transported, it is customary to define a quantity called mobility (u) as the velocity (v) imparted to a specific ion per unit of electrical field strength E/L or in symbols, $$u = vL/E \tag{1}$$

Where E is the voltage drop and L is the separation distance between electrodes. Mobility is a property of the ion which can be measured. If the mobility of the anion is $u_-$ and the mobility of the cathion is $u_+$, then the fraction of the total current carried by the ions is $$t_- = u_-/(u_- + u_+) \text{ and } t_+ = u_+/(u_- + u_+) \tag{2}$$

The fraction of the total current carried by the anions, $t_-$, and cations $t_+$, depends upon their respective mobilities. In general, these are different numbers. However, the important point is that the current is carried by ions in solution, the fraction depending on their mobility, and that anions such as insulin move to the anode and cations move to the cathode. The ions are moving because they are being produced in the vicinity of one of the electrodes and being consumed at the other, resulting in a flow of ions. It is not proper to think of the ions being attracted or repelled electrostatically to the electrodes, as electrons are in space. This means also that if an ion should find itself, for instance, on the side of the anode, facing away from the cathode, it will be neither attracted nor repelled from it because there is no current flowing in the vicinity: as current flows only between the electrodes.

The rate of movement of the ions depends upon the voltage across the cell, among other things. This, however, is a very desirable property because it allows one to control the rate of movement by controling a voltage. While it is difficult to change the physical or mechanical properties of a device, it is usually easy to change the voltage across a cell.

It is a feature of the present invention to provide an ionic drug delivery device working on the principles of both diffusion and electrophoresis (electrodiffusion) wherein the rate can be controlled electrically.

The transport of molecules from the combined forces of electrical and diffusive forces has been described by Planck and Nernst in the last century. For most situations, and especially for passive membranes, the treatment is still adequate (although now it is known to be inadequate for certain cellular and subcellular membranes). The behavior of molecules under free diffusion and electrophoresis can be summarized in the following partial differential equation.

$$\frac{\partial c}{\partial t} = \frac{uE}{L} \frac{\partial c}{\partial x} + D' \frac{\partial^2 c}{\partial x^2} \tag{3}$$

Where c is concentration of the transported molecule at some position, x, between the electrodes and at some time, t. For the other variable, u is the mobility of the ion, D' is its diffusion coefficient, and E is the electric field strength. The diffusion coefficient is primed because with a membrane it is different than for free diffusion $D' = D(1 - \partial \phi)$ where the factor $(1 - \partial \phi)$ incorporates this. With respect to the transport of insulin values for c, u and D will be those for insulin.

Solving this differential equation for the case of material transport across a membrane, for the steady state, the solution is given by equation (4).

$$J = \frac{uEc_i}{L}\left(\frac{U^2}{1 - U^2}\right) \quad (4)$$

Where J is the delivery rate (in g cm$^{-2}$ of membrane/sec$^{-1}$), where $c_i$ is the concentration of the drug (insulin) in the reservoir of the pump, and u is the mobility of the ion being transported, already defined. U is a function which depends on some parameters of the drug and on the delivery system. This is shown by equation (5).

$$U = e^{uEh/2LD'} \quad (5)$$

In this equation h is the thickness of the membrane.

For zero current density, equation (4) reduces to that for diffusion only. For currents resulting in pumping the drug out of the reservoir (negative currents), and for high current density, the function U in equation (5) is much larger than 1 and equation 4 reduces to $$J = \frac{uiCi}{S} \quad (6)$$

Here, i is the current density (in amperes cm$^{-2}$), and s is the specific conductivity of the medium containing the drug (in mho cm$^{-1}$). In this case, the specific delivery rate does not depend on the diffusion coefficient, D'. This means that, when operated at high current density, transport is by electrophoresis only and diffusion is not important.

For small currents, equation (4) reduces to $$J = c_i\left(\frac{U_i}{S} - \frac{D'}{h}\right) \quad (7)$$

This means that, for small current density, the specific delivery rate varies in a linear fashion with current density.

Figure 2:
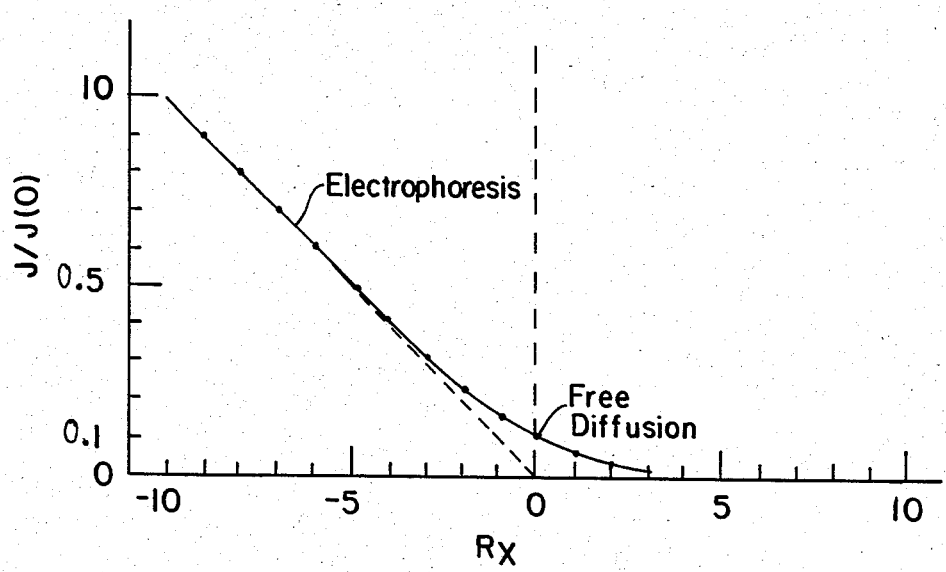
FIG. 2 is a plot of a relationship between diffusion and electrophoresis.

FIG. 2 is a dimensionless plot of equation (4) in which the specific delivery rate relative to the zero current rate (i.e., diffusion alone) is plotted against the function $R_x$. Here $R_x$ is a dimensionless function defined as uhi/SD'. $R_x$ depends upon constants of the system and current density. When the constants in equation (4) are known, FIG. 2 can be employed to calculate the fundamental relationships describing the operation of the pump for various drugs and for various operating conditions. It can be seen that for positive current ("pumping in"), the delivery rate is less than for diffusion alone and it rapidly approaches zero with increasing current. For negative current ("pumping out"), the delivery rate is larger than that for diffusion alone. In the linear portion of the curve, the pump is operating by electrophoresis primarily with diffusion not being significant.

A phenomenon called "polarization" generally prevents the use of electrodes such as carbon to produce a direct current although they would be acceptable with pulsed DC or alternating current. As soon as current begins to flow, the electrode products collect in the vicinity of the electrode surface and create a back voltage. Sometimes this back voltage is as high as the driving voltage and current will not flow. We have developed a method whereby this problem can be avoided in an electrophoretic pump. The degree of polarity depends upon the current density in the electrode surface. The half-time for decay of this polarity, however (with the electrodes shorted) does not. Since the region of the polarity about the electrode surface is very thin, the decay time is very short. This means that by making the electrodes with a very high surface area, total current can be high but current density at the electrode surface kept low. Further, it means that polarization will occur slowly and depolarization will be fast. Thus, we use a pulsed DC power system (as described hereinafter) in the pump, generating reasonable current while avoiding serious polarization problems. The current will flow until the polarization hits an upper limit, then will stop for a relatively short time to allow depolarization. Then, the cycle will repeat. Our experiments with porous graphite electrodes show that 5 milliamperes of current can flow for 1 minute before the voltage rises to 1 volt. The electrodes depolarize in about 10 seconds or less.

To create pulsed DC, the voltage across the membrane may be monitored through a comparator circuit. When the voltage reaches a predetermined value, the comparator output changes. The comparator output is used to turn off the DC source for a predetermined time. When the time is exhausted, the comparator output is reset, and the cycle resumes from the beginning. The curcuit resembles in operation a free running multivibrator (analog form) where the current charging a capacitor while monitoring the voltage and starts to discharge the capacitor when it reaches a certain value and stops discharge when it reaches other values.

Figure 3:
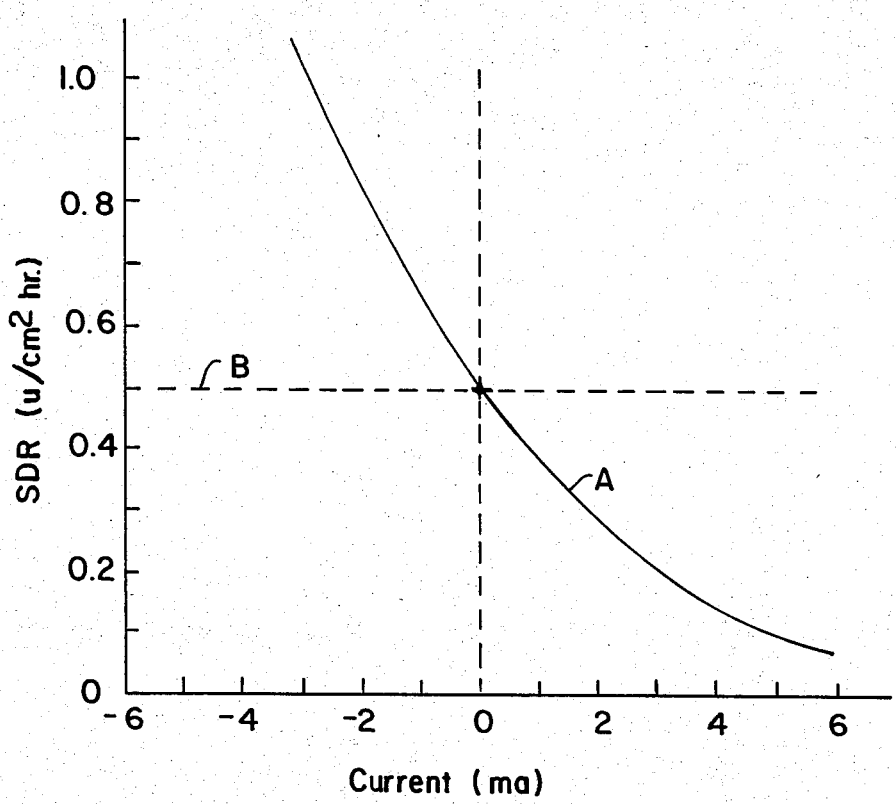
FIG. 3 is a plot of delivery rate versus current.

Shown in FIG. 3 is the relationship between the current resulting from a particular potential level applied to the electrodes as plotted against the specific delivery rate of the ionic drug. Plot A is a theoretically developed relationship. The minus current indication with respect to current is to represent electrode polarity as shown in FIG. 1 and the positive current is the reverse direction. When the current of the experimental system was at zero, diffusion was the sole means of transport of ionic material out of the reservoir. Ion transport was effected at the level B. In other words, without energizing the electrodes an ionic flow equal to 0.5 units of the ionic drug, (which in the experimental case was bovine serum albumen, which can readily be correlated with insulin), per square centimeter of passibe membrane area per hour resulted. When a negative potential is imposed on the electrodes a resultant current flows through the liquid between the electrodes. As the magnitude of the current is increased in the negative direction, the rate of delivery of the ionic material through the membrane is proportionately increased. When the current reaches the level of $-3$ milliamperes the rate of delivery increases from 0.5 units/cm$^2$/hrs to 1 unit cm$^2$/hr. Similarly, when the polarity of the electrodes is reversed, the current imposes a retarding effect as electrophoresis action tends to oppose the diffusion. As a result the net delivery area drops below the rate for diffusion without any imposed current. It is noted that the delivery rate did not reach zero even when the current reached 6 milliamperes.

Referring now to FIG. 4 there is shown the pump of one embodiment of the present invention. It has an exterior housing which is preferably sealed and provides suitable openings for refilling and discharge of ions. The housing is preferably made of a suitable inert material which will possess adequate strength. Among the suitable materials are titanium, medical grade stainless steel and reinforced polymers. The size and shape of the pump should be such that it is compatible with the portions of the body in which it will be implanted. In the form illustrated, the pump is generally triangular with rounded corners and has a top wall 32, a lateral wall 34 and a bottom wall (not shown) essentially identical to the top wall but without an opening. The top wall has filler opening 36 and the lateral wall defines discharge opening 38. In a preferred embodiment of the invention the pump will have an overall length L equal to about 90 mm to 110 mm, a height H equal to about 15 mm to 25 mm and width W equal to about 35 mm to 50 mm. Shown positioned within the top opening 36 is a self-sealing filler membrane 50 which will be described in greater detail hereinafter. Disposed within discharge opening 38 is the passive discharge membrane 52.

Figure 5:
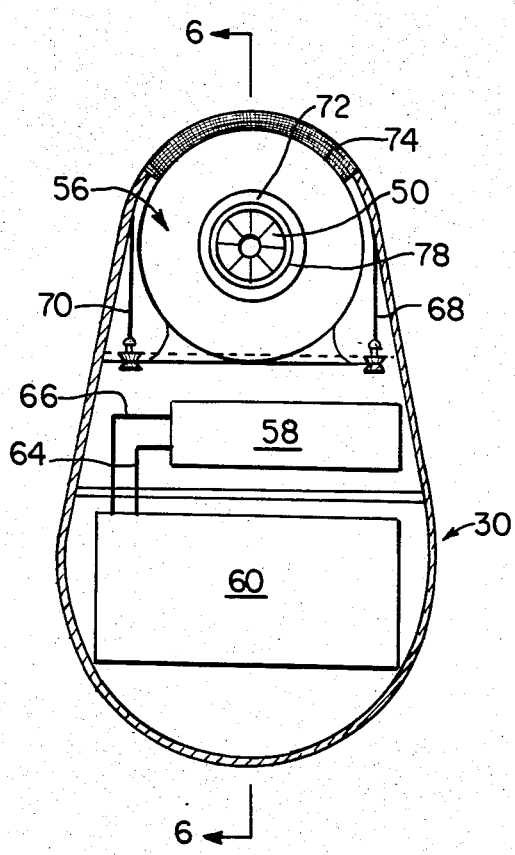
FIG. 5 is a partially schematic top plan view (with a top wall not shown) of an embodiment of the present invention.
Figure 6:
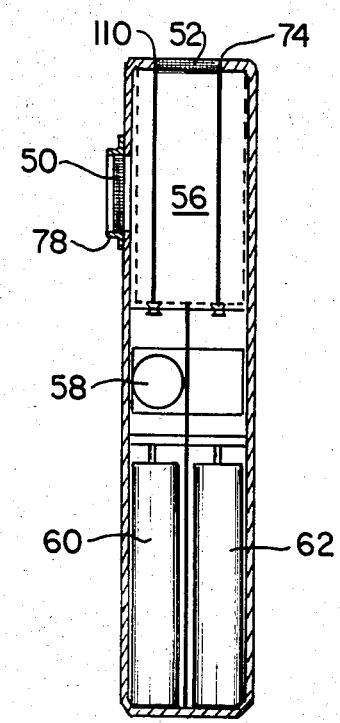
FIG. 6 is a cross-sectional illustration of the system of FIG. 5 taken through 6-6.

Referring now to FIGS. 5 and 6, the interior arrangement of the pump will be considered in greater detail. In general, in the form illustrated, the pump interior has three sections. The reservoir 56 is positioned at the narrow portion of housing 30, the electronic compartment 58 is disposed adjacent to the reservoir 56 and the batteries 60, 62 are positioned within the enlarged end of the housing. Electrical wires 64, 66 carry electricity from the batteries 60, 62 to the electronic unit 58 which includes a high value capacitor (on the order of about 3 to 5 farads, for example). These capacitors function as an electrical energy reservoir. This is needed because lithium iodide batteries do not provide the required current during periods of unusually high demand ("bolus") and they have a high internal impedance. These capacitors would not necessarily be required for batteries with low internal impedance such as $L_i$-CuS batteries, for example. Wires 68, 70 permit the batteries 60, 62 to energize the electrodes by way of electronics unit 58 (with the electrical connection between the two not illustrated). As is shown the wires 68, 70 are preferably wound around reservoir 56. These wires are used as antennas to transmit and receive information from an external programmer. Internally the signals may be fed through blocking capacitors to the communication circuitry.

The reservoir 56 provides a sealed chamber for storage of the ionic drugs. Preferably it has a storage capacity of about 15 to 25 ml. In the form illustrated, the reservoir is of generally cylindrical configuration and has an opening 72 in the upper wall which sealingly receives filler membrane 50 and an opening 74 in the lateral wall which receives the passive membrane 52. As is shown in FIG. 4, the membrane 50 is exposed through opening 36 in the top of the housing 32 and membrane 52 is exposed through opening 38 in the housing 32. In the form illustrated the housing openings 36, 38 and the corresponding resevoir openings 72, 74 are, respectively, disposed on surfaces oriented generally perpendicular to each other. This arrangement prevents piercing of the delivery port by the filler needle, thereby obviating the need for a needle target. For example, assuming the embodiment illustrated in FIG. 6 is surgically implanted in the peritoneum of the patient with the membrane 50 closely adjacent to and facing the skin, a minimum path of travel for a hypodermic syringe is provided for convenience in filling. Also, discharge of ions through the opening 52 will direct the ions into the surrounding tissue of the patient.

In order to minimize contact between the ionic drug or ionic drug containing solution or slurry with the interior walls of the reservoir 56 the interior may advantageously be provided with a suitable coating material such as silicone rubber, for example. A suitable material is that sold under the trade designation Silastic. If desired, an immobilized ionic group such as a suitable ion exchange resin may be employed to resist precipitation and adhesion of the ionic drug to the reservoir wall.

The present system is adapted to be operated at a low current level. This provides several advantages. It enables the use of batteries which under such service conditions will have a very long life, thereby minimizing the frequency with which the implantable device must be surgically removed in order to replace the batteries. Also, the pump housing may be maintained at the desired small size. A suitable type of battery for use in the present system is the lithium iodide cell which may have a voltage of about 2.7 volts (beginning of life) to about 2.1 volts (end of life). These batteries have proven to be successful in the connection with use in cardiac pacemakers. See generally, The Lithium Iodide Cell—History by Dr. Alan A. Schneider et al., Medical Electronic & Data, January-February 1977, pp. 48–51.

As the electronic means 58 may take the form of known solid state systems or any alternate means which would be readily apparent to those skilled in the art, a detailed disclosure of the same need not be provided herein. Also, numerous external programmers are known to those skilled in the art. See generally Christionsen et al., J. Clinical Lab. Invest. 41(z), pp. 674–654 (November 1981); Geisen et al., Res. Exp. Med. (Bev); 179(2), pp. 103–111, 1981; and W. Burns et al. Inn. Med. 36(17), pp. 625–627 (September 1981). In general, such systems involve setting a basal program based on timing principals such that the batteries 60, 62 of the present system will energize the electrodes adjacent membrane 52 at a certain current level for a predetermined period of time at predetermined times during the day. At times the system will either be at an "off state" wherein transport of ions continues by diffusion only. Also, an emergency or larger demand situation ("bolus") may be provided for. In addition, in the emergency situation the patient may activate the system so as to provide a single cycle of operation at a predetermined emergency or bolus level to dispense additional quantities of the ionic drugs, such as during meal times, for example. One manner in which this might be accomplished is by having the patient hold a magnet in close proximity to the unit for a predetermined time.

As a convenient means for providing extra insulin, for example to avert hyperglycemia, this externally activatible bolus system may have a magnetic reed switch in the electrical circuit of the pump. The switch when in "off" position may be moved to the "on" position by application of a magnetic field of a predetermined minimum intensity for a predetermined period. This minimizes the risk of accidental triggering of the pump by stray magnetic fields. In general, the programming is so established as to preclude emergency activation beyond the given number of times within a twenty-four hour period in order to prevent overdosing of the patient. It is also preferable, in general, to have the programmer such that it can be programmed only by the physician and not by the patient.

In providing insulin to a diabetic patient, for example, the average daily dose will be about 1 unit/kg of body weight. A unit of insulin is about 1/24 mg. A patient requires about 40 to 80 units a day. The pump will be set to deliver a portion of this by diffusion with the electrodes not energized and a portion to be delivered electrophoretically, with possible additional energizing amounts delivered by bolus action. The reservoir will preferably hold about a 250 day supply for an average patient.

Referring once again to FIG. 5, in the filler opening 72 a plurality of radially oriented reinforcement struts 78 are preferably molded into the membrane in order to reinforce the same.

Figure 7:
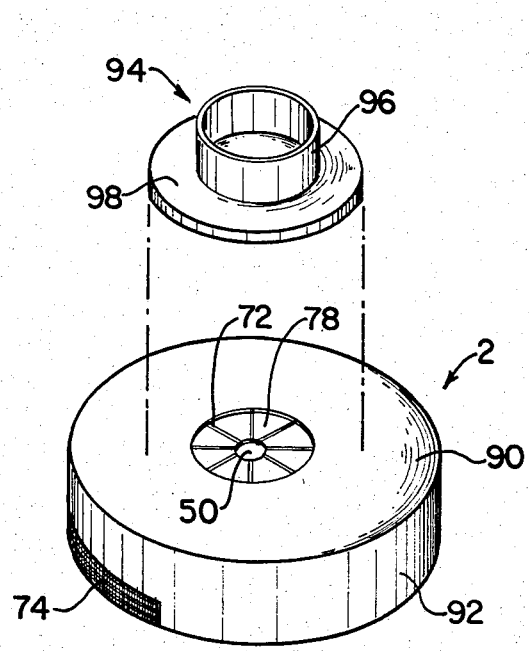
FIG. 7 is an exploded view of a form of collar and reservoir of the camptioned invention.
Figure 8:
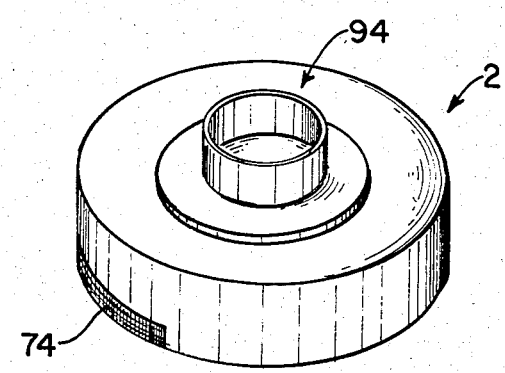
FIG. 8 is a generally cylindrical form of reservoir of the present invention.
Figure 9:
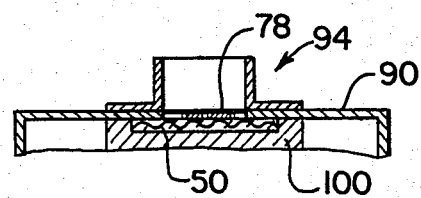
FIG. 9 is a partially exploded cross-sectional illustration of a form of filler membrane assembly of the present invention.

FIGS. 7 through 9 show further refinements of a preferred reservoir arrangement. The reservoir 2 has the upper wall 90 which contains opening 72 and the filler membrane 50. A lateral wall 92 is provided with the discharge opening 74 and a bottom wall (not shown) which is substantially of the same size and shape as the top wall 90 and may be imperforate. As is shown in the exploded view of FIG. 7, a collar member 94 is provided with a tubular portion 96 and a lower radially extending flange portion 98. The flange portion 98 is adapted to be secured to the upper wall 90 such that the bore of tube 96 is generally aligned with opening 72. After positioning of the membrane in place and securement of the member 94, the upper portions of the collar tube 96 are deformed downwardly and inwardly over the membrane 50. This securement may be effected by any desired means such as adhesive bonding. Collar 94 facilitates manual location of membrane 50 for refilling.

FIG. 9 shows a convenient means of creating the membrane construction. A mold member 100 having an upwardly facing recess is placed in underlying contacting relationship with respect to wall 90. The strut members 78 are placed in the desired reinforcing position and the membrane material in molten state is poured into the assembly so as to create the desired structure. This serves to seal the opening 72 while permitting penetration therethrough by a hypodermic syringe employed to refill the reservoir. As is shown in FIG. 6, a membrane frame 110 is adapted to hold the electrode membrane assembly which permits discharge of ions through opening 74.

Figure 10:
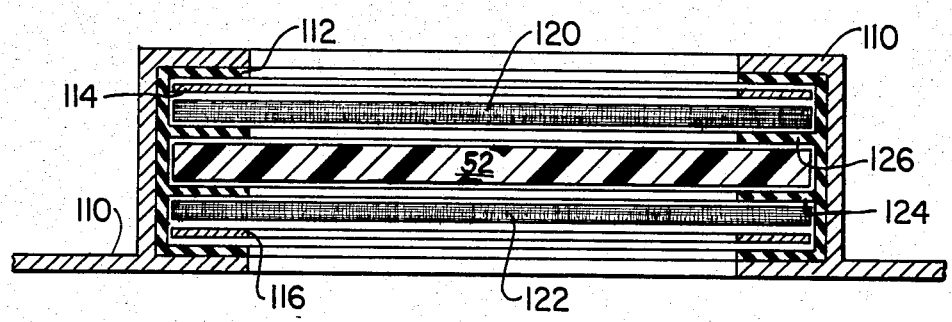
FIG. 10 is a fragmentary cross-sectional view showing a portion of the discharge opening of the reservoir.

Referring to FIG. 10, details of the preferred assembly and the discharge opening 74 will be considered. The reservoir, which may advantageously be made of a suitable metal such as titanium, has the protective titanium shroud 110 secured to the peripheral wall 92 thereof in surrounding relationship with respect to the membrane 52. The assembly, which consists of a pair of porous electrodes and interposed passive ionic membrane which permits passage of ions, will be considered. A generally channel shaped electrically insulative frame 112 which may be made of polytetraflouroethylene, secures a pair of metal frame members 114, 116. A pair of carbon mesh electrodes 120, 122 are positioned inwardly of the frame members 114, 116. The membrane 52 is separated from the electrodes 120, 122 by suitable annular electrical insulators 124, 126. A suitable adhesive may serve to both seal and secure the assembly lead. Electrical leads from the battery 60, 62 by way of the electronics means 58 serve to energize the electrodes with one lead functioning as a positive electrode and the other as a negative electrode. In those instances where a negative ionic drug is being dispensed by the pump the innermost electrode 120 will have a negative charge and the outermost will have a positive charge. The electrodes will produce an electrochemical potential gradient, as these ions carry a net charge, they are subjected to forces which cause them to move to the field. The anions move to the anode and cations to the cathode.

Figure 11:
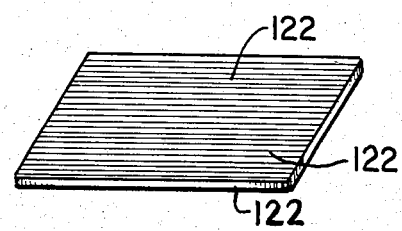
FIGS. 11 through 13 show sequential stages of a method of making a porous electrode of the present invention.
Figure 12:
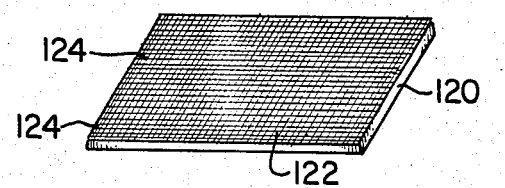
Figure 13:
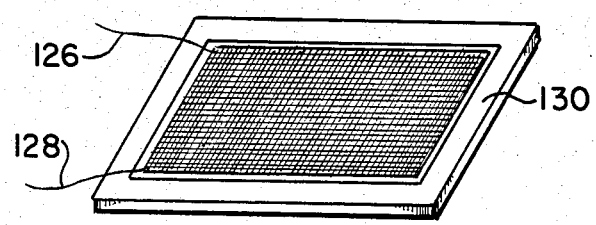

Referring to FIGS. 11 through 13 a method of making a porous electrode for use in the present invention will be considered. The porous electrode provides the advantage of increased surface area. A suitable electrically insulative support material such as polytetrafluoruethylene, medical grade, epoxy or silicone rubber, for example, 120 is provided. A series of electrically conductive members 122, such as carbon fibers, preferably having a thickness of about 1 to 10 microns are positioned on the upper surface of support 120 with the fibers being generally parallel to each other. A second series of electrically conductive fibers 124 are positioned in relative parallel relationship with respect to each other and are oriented generally perpendicularly with respect to the other series of fibers 122. An electrically conductive frame member 130 composed of a material such as platinum, medical grade stainless steel or carbon paste, for example, is then secured in electrically conductive overlying relationship with respect to underlying mesh of fibers 122, 124. Lead wires 126, 128 from the electronics unit 58 are electrically connected to the mesh of fibers 122, 124 through the conductive frame 130. A pair of such frames is used in the construction shown in FIG. 10.

Figure 14:
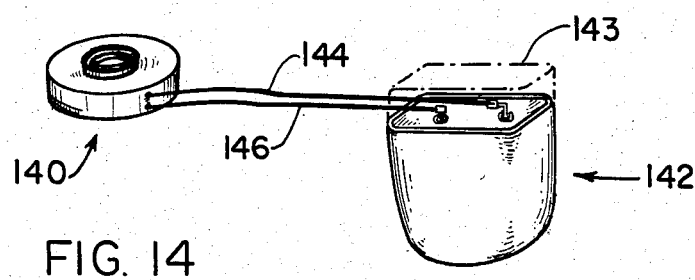
FIG. 14 is a schematic illustration of another embodiment wherein the reservoir is positioned exteriorly of the housing.

Referring to FIG. 14, an alternate embodiment of the invention will now be considered. In this embodiment the reservoir 140 rather than being positioned within the housing 142 is remotely positioned with respect thereto and is in electrical communication with the electronics units and batteries disposed within the housing 142 by means of electrical leads 144, 146. A suitable covering layer 143 (dotted) is provided on housing 142 and may be a silicone rubber, for example.

As has been indicated hereinbefore, various means of effecting electronically controlled triggering of the electrophoretic action to either boost or retard ionic drug delivery may be employed. A preferred approach of the present invention involves control of pumping of the ionic drug by means of an essentially constant current applied to the electrodes for a predetermined time. The time-current combination may be equated, for a given ionic drug, with a predetermined quantity or dosage to be delivered. For example, if it has been determined that 0.10 unit of insulin will be delivered by the pump when the current is at a given current level such as about 1 to 10 milliamps, and the pump is energized for a given period of time such as 25 to 35 seconds, the remote programmer will establish a 24 hour program for the pump wherein the given amount of units desired to be delivered within that time will be delivered by using multiples of the 0.10 unit. Further, this is employed to space the dosage delivery in the desired fashion.

Figure 15:
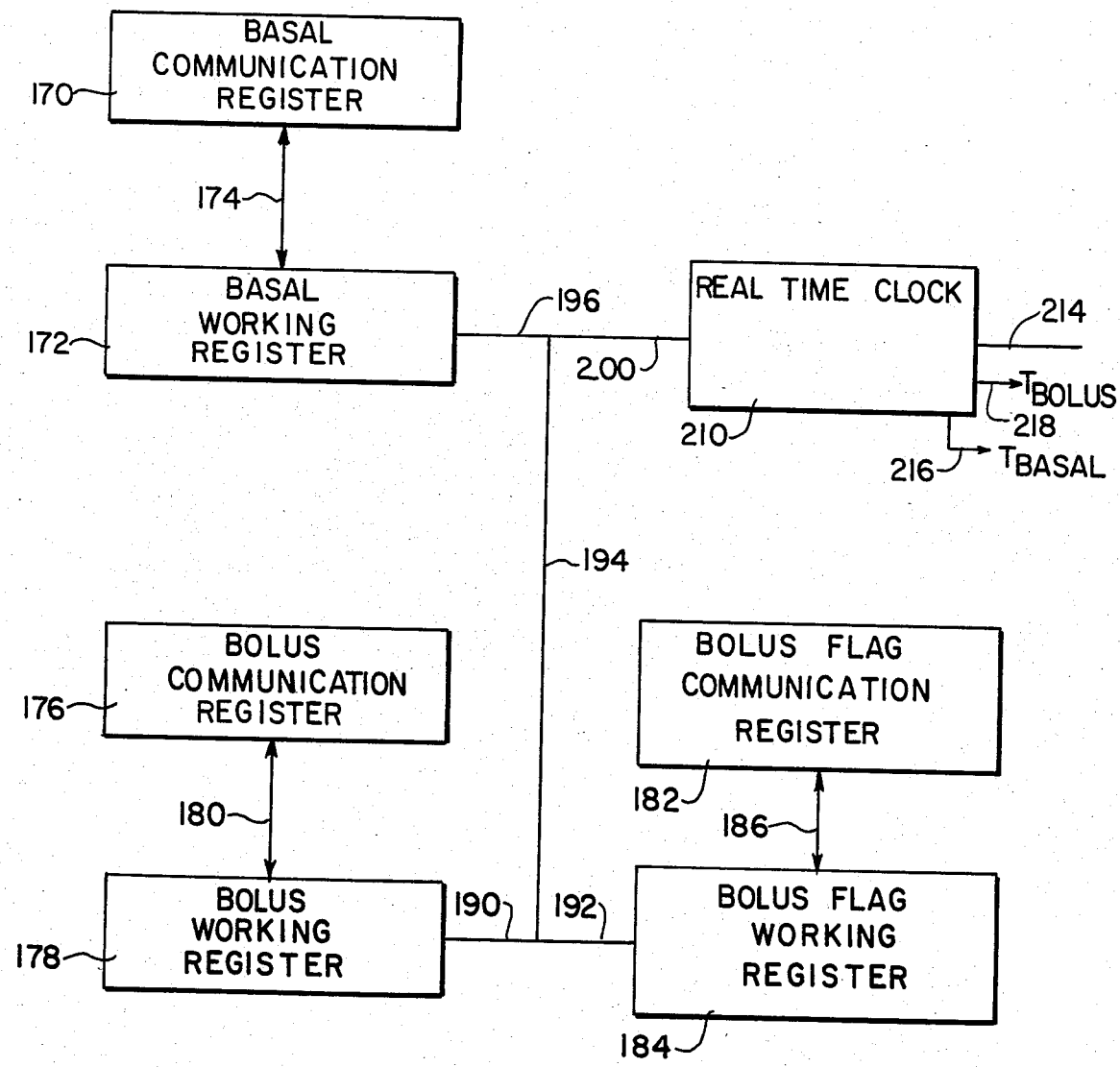
FIG. 15 is a schematic illustration of a portion of the electronic components of the pump.

Referring to FIG. 15, a modular unit of the electronic system of the pump and the paths of information flow will be considered. The schematic illustrated may involve a given unit of time such as two hours, for example, with twelve duplicate units being provided to cover a day. In operation, the programmer will send a radio signal which will be received by the basal (regular) demand communication register 170 and the bolus (unusual) communication register 176. The former will be provided with a signal telling it how many pulses of 0.1 units of insulin to deliver within a given time period such as two hours, for example. The latter will receive a signal telling it how many pulses of 1.0 units of insulin to deliver once it has been activated by the patient as for example, before a meal. The real time clock 210 serves to provide a time reference for operation of the basal delivery system. When the designated time for activation of the basal system has been reached the information regarding the time period during which the system will operate is transferred from the basal working register 172 by means of path 174. Each working register 172, 178, 184 cooperates with an associated communication register and communicates respectively by paths 174, 180, 186 with registers 170, 176, 182, which in turn are in receipt of signals from the external programmer. This system will permit the batteries to energize the electrodes so as to impose the current desired for the predetermined period of time which will be governed by the real time clock 210. At the end of the cycle of operation, energization of the electrodes will be terminated. Information regarding the initial quantity of the ionic drug present in the reservoir as well as the amount discharged through basal or bolus action may be stored in a separate counter. It is also desirable to have the programmer receive, upon request, signals providing information regarding the amount of material left in the reservoir. This is determined by counting the delivery pulses. This register is cleared only after refilling of the reservoir in order to give a cumulative reading of the amount of material remaining. In this way the demands for individual patients for insulin can be established.

The expression $T_{basal}$ and $T_{bolus}$ are the times required to deliver, respectively, the basal and bolus levels. The times will generally consist of a certain number of pulses such as, for example, 28 seconds for basal and 280 seconds for bolus.

In a bolus situation, a magnetic field is applied to the pump at a predetermined intensity for a given period of time in order to initiate movement of the magnetic reed switch so as to cause a signal to be transferred from bolus working register 178 to the output counter. Information is placed in the bolus flag communication register 182 during programming and transferred to the working register 178. The bolus flag working register 184 permits the bolus system to be activated only a predetermined number of times during the day in order to avoid the patient dispensing an excess amount of insulin by bolus activation. For example, if it were determined that a patient should be permitted a maximum of four bolus cycles per day, each time the flag working register 184 is set by the programmer and the magnet reed switch is activated by the patient, the bolus delivery is initiated. The delivery is terminated after a preselected number of pulses. The real time clock 210, is connected to the respective working registers 172, 178, 184, respectively by paths 196–200, 190–194–200 and 192–194–200. The real time clock 210 will have a counter which serves to automatically control the duration of a bolus or basal cycle. When the counter reaches zero the delivery by electrophoretic action would be terminated.

If desired, a glucose sensor may be provided so as to permit sensing of the glucose content of blood and providing a servo control to adjust the operation of the pump for departures from desired glucose blood level ranges.

If it is desired to provide a pump wherein diffusion is either extinguished or substantially minimized during periods when the pump is not energized electrically, an active membrane such as an ion exchange membrane, for example, may be used as the diffusion membrane.

While not preferred, if desired one could eliminate the basal rate or reduce it to zero and rely solely on bolus distribution.

It will be appreciated that the present invention provides a self contained, refillable, externally programmable, implantable ionic drug diffusion device which is economical to use, will be of long duration through the low power required and is of high reliability as a result of its lack of mechanical moving parts which would be subject to wear and tear.

While for simplicity of disclosure reference has been made previously to use of the pump with a single ionic drug, it will be appreciated that it may be used with two or more materials simultaneously.

Whereas particular embodiments of this invention have been described above for purposes of illustration, it will be evident to those skilled in the art that numerous variations of the details may made without departing from the invention as defined in the appended claims.

We claim:

1. An implantable electrophoretic pump for ionic drugs comprising
    a housing,
    a substantially fixed volume reservoir for storing said ionic drugs having a filler opening and a discharge opening,
    said housing having opening means disposed generally adjacent to said filler opening and said discharge opening,
    a filler member disposed within said filler opening and being self-sealing and adapted to be pierced by a reservoir filling member and upon removal of said filling member will resist leakage therethrough,
    a reservoir discharge member disposed within said discharge opening and having a diffusion membrane and a pair of associated electrodes,
    electrical energizing means for energizing said electrodes, and
    the polarity of said electrodes being adapted to be connected such that when said electrodes are energized increased flow of said ionic drug through said discharge member will occur as compared with flow induced solely through diffusion when said electrodes are not energized, whereby said pump can deliver said ionic drugs electrophoretically.

2. The implantable electrophoretic pump of claim 1 wherein said electrical means includes battery means.

3. The implantable electrophoretic pump of claim 2 wherein said diffusion membrane is a passive diffusion membrane.

4. The implantable electrophoretic pump of claim 1 including said discharge member being in communication with the exterior of the housing through said opening means, and
    said filler member being in communication with the exterior of said housing through said opening means.

5. The implantable electrophoretic pump of claim 3 including said passive diffusion membrane permitting the passage of said ionic drug therethrough under the influence of diffusion or electrophoresis or both.

6. The implantable electrophoretic pump of claim 1 including said diffusion membrane being an active membrane.

7. The implantable electrophoretic pump of claim 6 including said active membrane being an ion exchange membrane.

8. The implantable electrophoretic pump of claim 5 including said filler opening being disposed in a first wall of said reservoir, and
   said discharge opening being disposed in a second wall of said reservoir.

9. The implantable electrophoretic pump of claim 8 including said first wall and said second wall being substantially perpendicular to each other.

10. The implantable electrophoretic pump of claim 5 including said electrodes being of porous construction.

11. The implantable electrophoretic pump of claim 5 including said electrodes being composed of a material selected from the group consisting of silver/silver chloride, carbon, carbon mesh and platinum.

12. The implantable electrophoretic pump of claim 5 including said reservoir having a chamber with a storage volume of about 15 to 25 milliliters.

13. The implantable electrophoretic pump of claim 5 including the interior of said reservoir except for the regions of said filler opening and said discharge opening having an interior coating of a material selected from a group consisting of resinous plastic and silicon rubber.

14. The implantable electrophoretic pump of claim 5 including electronic means energized by said battery means for energizing said electrodes during predetermined periods.

15. The implantable electrophoretic pump of claim 10 including electronic means having means for bolus activation which when activated is adapted to deliver additional quantities of said ionic drug.

16. The implantable electrophoretic pump of claim 15 including said bolus means adapted to be activated by means disposed exteriorly of the user.

17. The implantable electrophoretic pump of claim 14 including said electronic means having means for reversing the polarity of said electrodes.

18. The electrophoretic pump of claim 17 wherein said electronic means have means for charging the said electrode disposed closer to the interior of said reservoir with a charge of the type possessed by said ionic drug.

19. The implantable electrophoretic pump of claim 5 including said housing having an average height of about 15 to 25 mm., a maximum length of about 90 to 110 cm. and an average width of about 35 to 50 mm.

20. The implantable electrophoretic pump of claim 5 including said membrane being a passive membrane and said membrane being selected from the group consisting of cellulose esters, cellulose acetate, nylon polyvinylidene fluoride, polytetraflouroethylene and cellulose nitrates.

21. The implantable electrophoretic pump of claim 20 including said passive membrane having a thickness of about 100 to 200 microns and an area of about 0.5 to 5 $cm^2$.

22. The implantable electrophoretic pump of claim 5 including said reservoir being substantially cylindrical, and
   said filler opening being disposed on one of the end walls.

23. The implantable electrophoretic pump of claim 22 including said discharge opening being disposed in a lateral wall of said reservoir.

24. The implantable electrophoretic pump of claim 23 including said housing having a generally triangular shape in plan.

25. The implantable electrophoretic pump of claim 1 including
   said reservoir disposed within said housing.

26. The implantable electrophoretic pump of claim 1 including
   said reservoir disposed externally of said housing and being in electrical communication therewith.

27. The implantable electrophoretic pump of claim 14 including said electronic means including capacitor means.

28. The implantable electrophoretic pump of claim 13 wherein said material is an ion exchange resin.

29. A reservoir for an implantable electrophoretic pump including
   a hollow body defining a substantially fixed volume drug storage chamber,
   a filler opening defined within said body,
   a self-sealing member sealingly secured within said filler opening,
   a discharge opening defined within said body,
   a diffusion membrane sealingly secured within said discharge opening, and
   a pair of electrodes having an electrode disposed on each side of said diffusion membrane whereby said reservoir can deliver said drug electrophoretically.

30. The reservoir of claim 29 including said diffusion membrane being a passive membrane.

31. The reservoir of claim 29 including said diffusion membrane being an active membrane.

32. The reservoir of claim 29 including said diffusion membrane being an ion exchange membrane.

33. The reservoir of claim 29 including said reservoir body being of substantially rigid construction.

34. The reservoir of claim 33 including said filler opening being in a wall oriented generally perpendicularly with respect to the wall in which said discharge opening is defined.

35. The reservoir of claim 34 including said reservoir being of generally cylindrical shape.

36. The reservoir of claim 30 including said passive membrane being of a material selected from the group consisting of cellulose esters, cellulose acetate, nylon, polyvinylidene flouride, polytetraflouroethylene and cellulose nitrates.

37. The reservoir of claim 35 including said passive membrane having a thickness of about 100 to 200 microns.

38. The reservoir of claim 37 including said passive membrane having an area of about 0.5 to 5 $cm^2$.

39. The reservoir of claim 37 including resilient member having reinforcing members.

40. A method of delivering an ionic drug within a patient comprising
   providing an implantable electrophoretic pump having a housing within which is disposed a substantially fixed volume ionic drug storage reservoir having a filler opening sealed by a self-sealing membrane and a discharge opening sealed by a diffusion membrane having electrode means disposed on opposite sides of said diffusion membrane,
   introducing an ionic drug into said reservoir,
   implanting said pump in said patient,
   effecting basal rate delivery of said ionic drug to said patient by diffusion, and periodically energizing said electrode to effect alteration of the diffusion induced flow of ions out of said reservoir whereby said drug can be delivered electrophoretically.

41. The method of claim 40 wherein said diffusion membrane is a passive membrane.

42. The method of delivering an ionic drug of claim 40 including introducing said ionic drug into said reservoir prior to implantation of said pump.

43. The method of delivering an ionic drug of claim 40 including introducing said ionic drug into said reservoir after implantation of said pump.

44. The method of delivering an ionic drug of claim 40 including implanting said pump in said patient's peritoneum.

45. The method of delivering an ionic drug of claim 42 including providing electronic means operatively associated with said electrode means within said pump, and batteries disposed within said pump for energizing said electrodes.

46. The method of delivering an ionic drug of claim 45 including maintaining a substantially continuous flow of said ionic drug out of said reservoir by means of diffusion, and periodically enhancing or retarding said diffusion rate of flow through energizing said electrodes.

47. The method of delivering an ionic drug of claim 46 including reversing polarity of said electrodes when it is desired to retard diffusion induced flow of said ionic drug.

48. The method of delivering an ionic drug of claim 47 including periodically replenishing the supply of said ionic drug by introducing a hypodermic needle into said reservoir through said self-sealing membrane.

* * * * *

UNITED STATES PATENT AND TRADEMARK OFFICE
CERTIFICATE OF CORRECTION

PATENT NO. : 4,639,244

DATED : January 27, 1987

INVENTOR(S) : NABIL I. RIZK and CHARLES L. STEVENS

It is certified that error appears in the above-identified patent and that said Letters Patent is hereby corrected as shown below:

Column 2, line 61, "camptioned" should be --captioned--.

Column 3, line 47, "electodes" should be --electrodes--.

Column 5, line 10, "te" should be --the--.

Column 8, line 26, "curcuit" should be --circuit--.

Column 8, line 45, "passibe" should be --passive--.

Column 13, line 28, "expression" should be --expressions--.

Column 14, line 18 "may made" should read --may be made--.

Claim 20, column 15, line 53, a comma --,-- should be inserted after "nylon".

Signed and Sealed this

Fifth Day of April, 1988

Attest:

DONALD J. QUIGG

*Attesting Officer*      *Commissioner of Patents and Trademarks*